US011241159B2

(12) United States Patent
Torihama et al.

(10) Patent No.: US 11,241,159 B2
(45) Date of Patent: Feb. 8, 2022

(54) FLUID BLADDER, FLUID BLADDER MANUFACTURING METHOD, BLOOD PRESSURE MEASUREMENT CUFF, AND BLOOD PRESSURE MONITOR

(71) Applicant: OMRON HEALTHCARE Co., Ltd., Kyoto (JP)

(72) Inventors: Takashi Torihama, Kyoto (JP); Ryosuke Doi, Kyoto (JP); Yoshihide Tokko, Kyoto (JP); Eisuke Yamazaki, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 524 days.

(21) Appl. No.: 15/879,193

(22) Filed: Jan. 24, 2018

(65) Prior Publication Data
US 2018/0146867 A1 May 31, 2018

Related U.S. Application Data

(63) Continuation of application No. PCT/JP2016/058837, filed on Mar. 18, 2016.

(30) Foreign Application Priority Data

Jul. 24, 2015 (JP) ................. 2015-146947

(51) Int. Cl.
*A61B 5/022* (2006.01)
*A61B 5/00* (2006.01)
*A61B 5/024* (2006.01)

(52) U.S. Cl.
CPC ........ *A61B 5/02233* (2013.01); *A61B 5/6824* (2013.01); *A61B 5/742* (2013.01); *A61B 5/022* (2013.01); *A61B 5/024* (2013.01)

(58) Field of Classification Search
CPC ........................... A61B 5/022; A61B 5/02233
See application file for complete search history.

(56) References Cited

U.S. PATENT DOCUMENTS

| 5,193,549 A | 3/1993 | Bellin et al. |
| 2013/0053707 A1* | 2/2013 | Mirisoloff .......... A61B 5/02233 600/499 |

(Continued)

FOREIGN PATENT DOCUMENTS

| JP | H11-313805 A | 11/1999 |
| JP | 2003-024286 A | 1/2003 |

(Continued)

OTHER PUBLICATIONS

International Search Report issued in PCT/JP2016/058837, dated Jun. 14, 2016 (2 pages).

(Continued)

*Primary Examiner* — Puya Agahi
(74) *Attorney, Agent, or Firm* — Osha Bergman Watanabe & Burton LLP

(57) ABSTRACT

A fluid bladder includes multiple segment bladders that are each formed by folding one sheet in half in a width direction X extending along an artery passing through the measurement site, welding or adhering edge portions on a side opposite to the folding location for folding in half, and welding or adhering edge portions in a lengthwise direction Y. The multiple segment bladders are stacked in a width direction orthogonal to the measurement site and integrated, and the folding locations are arranged alternatingly on opposite sides in the width direction.

11 Claims, 12 Drawing Sheets

(56) References Cited

U.S. PATENT DOCUMENTS

2013/0053708 A1\* 2/2013 Quinn ................ A61B 5/02233
                                                        600/499
2015/0182138 A1\* 7/2015 Yoshino ............. A61B 5/02233
                                                        600/499
2018/0153418 A1\* 6/2018 Sullivan ............. A61B 5/02225

FOREIGN PATENT DOCUMENTS

| JP | 2006-158876 A | 6/2006 |
|----|---------------|--------|
| JP | 2006-174860 A | 7/2006 |
| JP | 3168376 U     | 6/2011 |
| JP | 3168377 U     | 6/2011 |

OTHER PUBLICATIONS

Written Opinion issued in PCT/JP2016/058837, dated Jun. 14, 2016 (3 pages).

\* cited by examiner

FLUID BLADDER, FLUID BLADDER MANUFACTURING METHOD, BLOOD PRESSURE MEASUREMENT CUFF, AND BLOOD PRESSURE MONITOR

TECHNICAL FIELD

Embodiments of the present invention relate to a fluid bladder, and more specifically relate to a fluid bladder that is provided in a blood pressure measurement cuff in order to compress a measurement site.

Also, an advantage of one or more embodiments of the present invention relates to a fluid bladder manufacturing method for manufacturing such a fluid bladder.

Also, one or more embodiments of the present invention relate to a blood pressure measurement cuff that includes such a fluid bladder and that compresses a measurement site.

Also, one or more embodiments of the present invention relate to a blood pressure monitor that includes such a blood pressure measurement cuff.

BACKGROUND ART

Conventionally, as disclosed in Patent Document 1 (JP 3168376U) for example, a fluid bladder of this type has been known which is constituted by a first fluid bladder and a second fluid bladder that are stacked and are in communication with each other, and specifically is constituted such that the cross-sectional shape when cut along the width direction is approximately "8"-shaped. The cuff including this fluid bladder is attached by being wrapped around a rod-shaped measurement site such as an arm.

CITATION LIST

Patent Literature

Patent Document 1: JP 3168376U

SUMMARY OF INVENTION

With the cuff including the above-described fluid bladder, when inflated due to a fluid (e.g., air) being supplied to the fluid bladder, the stroke amount (swelling distance) in the stacking direction (thickness direction) is increased compared to the case of being simply composed of one fluid bladder, and therefore it is thought that the fluid bladder can be compressed.

However, with the cuff including the above-described fluid bladder, the thickness of a central region corresponding to the center of the "8" of the fluid bladder in the width direction is thinner compared to the thickness of the other regions. For this reason, with the cuff including the fluid bladder, in the entire cuff width, a pressure distribution is present in which the pressure at the central region corresponding to the center of the "8" of the fluid bladder is high and the pressure gradually decreases moving away from the central region. If the pressure gradually changes in the width direction in this manner, a phenomenon occurs in which, for example, the blood flow enters partway in the entire cuff width and stops immediately before the central region. For this reason, with measurement using an oscillometric method, for example, noise is generated in the cuff pressure signal, and with a Korotkoff method, noise is generated in the Korotkoff sound signal and the blood pressure value measurement accuracy decreases, which is problematic. For example, if the width direction dimension is set to be smaller for the purpose of reducing the size of the cuff, this problem worsens.

Here, an advantage of one or more embodiments of the present invention lies in providing a fluid bladder that is provided in a blood pressure measurement cuff in order to compress a measurement site, and that can flatten a blood pressure distribution in a width direction extending along an artery that passes through a measurement site.

Also, an advantage of one or more embodiments of the present invention lies in providing a fluid bladder manufacturing method for manufacturing such a fluid bladder.

Also, an advantage of one or more embodiments of the present invention lies in providing a blood pressure measurement cuff that includes such a fluid bladder.

Also, one or more embodiments of the present invention provide a blood pressure monitor that includes such a blood pressure measurement cuff.

Therefore, a fluid bladder according to one or more embodiments of the present invention is a fluid bladder provided in a blood pressure measurement cuff in order to compress a measurement site, including:

a plurality of segment bladders, each segment bladder being formed by folding one sheet in half in a width direction extending along an artery passing through the measurement site, welding or adhering edge portions on a side opposite to the folding location for folding in half, and welding or adhering edge portions in a lengthwise direction orthogonal to the width direction, wherein the plurality of segment bladders are stacked in a width direction orthogonal to the measurement site and integrated, and the folding locations are arranged alternatingly on opposite sides in the width direction.

In the present specification, "edge portion" indicates a region of a certain range including an edge. "Edge portions" being "welded or adhered" means that at least a portion of this region is welded or adhered.

Being "integrated" means being made inseparable from each other, and for example, means that half-sheets that are adjacent to each other in segment bladders that are adjacent to each other are welded or adhered. Note that "half-sheets" indicate sheets that are substantial halves of a sheet that is segmented (or is to be segmented) at a folding location.

With the fluid bladder according to one or more embodiments of the present invention, the segment bladders are each formed by folding one sheet in half in the width direction extending along the artery that passes through the measurement site, welding or adhering the edge portions on the side opposite to the two folding locations, and welding or adhering the edge portions in the lengthwise direction orthogonal to the width direction. Accordingly, the segment bladders have so-called teardrop-shaped cross-sections when inflated due to fluid being supplied thereto. Here, with the fluid bladder, the multiple segment bladders are stacked in the thickness direction orthogonal to the measurement site, and the folding locations for folding in half are alternatingly arranged on opposite sides in the width direction. Accordingly, for example, in the region of one end side in the width direction of the fluid bladder, the relatively thick portion of the odd-numbered segment bladder and the relatively thin portion of the even-numbered segment bladder adjacent thereto are stacked alternatingly. As a result, in the region on the one end side, the overall thickness of the multiple segment bladders is made uniform. In the central region in the width direction of the fluid bladder, the portions with intermediate-level thicknesses of the multiple segment bladders are stacked. As a result, in the central region, the overall thickness of the multiple segment bladders is made uniform. Also, in the region on the other end side in the width direction of the fluid bladder, in the thickness direction, the relatively thin portion of the odd-numbered segment bladder and the relatively thick portion of the even-numbered segment bladder adjacent thereto are alternatingly stacked. As a result, in the region on the other end side, the overall thickness of the multiple segment bladders is made uniform. Accordingly, with this fluid bladder (and accordingly, the cuff including the fluid bladder), the pressure distribution on the measurement site is flattened in the width direction. Also, since the multiple segment bladders are integrated, the multiple segment bladders do not become misaligned from each other in the width direction, for example. As a result, even if the fluid bladder (and accordingly, the cuff including the fluid bladder) is repeatedly inflated and deflated, the flat pressure distribution is maintained in the width direction.

Note that with this fluid bladder, the multiple segment bladders are stacked in the thickness direction, and therefore, similarly to the conventional example of the fluid bladder, the stroke amount (swelling distance) in the thickness direction is increased compared to the case of being simply composed of one bladder, and the measurement site can be compressed.

With the fluid bladder of an embodiment,
through holes that enable air to flow between segment bladders that are adjacent to each other are provided in inner regions of half-sheets that are adjacent to each other in the segment bladders that are adjacent to each other, and
the half-sheets that are adjacent to each other are integrated by being welded or adhered such that the through holes are surrounded.

Here, the "inner region" of a half sheet indicates a region of the interior excluding the folding location, the edge portions in the width direction, and the edge portions in the lengthwise direction orthogonal to the width direction.

With the fluid bladder of this embodiment, the fluid can flow through the through hole between the segment bladders adjacent to each other. Accordingly, if the fluid is supplied from an external supply source to one segment bladder for example, the fluid can be supplied to all of the multiple segment bladders. The half-sheets adjacent to each other are welded or adhered such that the through hole is surrounded, and therefore leakage of the fluid from the through hole through the gap between the half-sheets adjacent to each other is prevented.

With the fluid bladder of an embodiment, a nipple for introducing and/or discharging fluid for compressing the measurement site is attached to a half-sheet of the plurality of segment bladders that is arranged on a side located farthest from the measurement site.

With the fluid bladder of this embodiment, if the fluid is introduced to the segment bladder on the farthest side through the nipple, the fluid can flow through the through hole between the segment bladders as described above, and therefore the fluid can be supplied to all of the multiple segment bladders. Conversely, the fluid cannot be emitted from all of the multiple segment bladders through the nipple.

With the fluid bladder of an embodiment, the number of segment bladders stacked in the thickness direction is even.

The measurement site is substantially cylindrical rod-shaped and has an outer diameter that is substantially constant from the base end side through which the artery passes (the side near the measurement subject's heart) to the terminal end side (the side far from the measurement subject's heart). Here, with the fluid bladder of this embodiment, since the number of segment bladders stacked in the thickness direction is even, the overall thickness of the multiple segment bladders is substantially constant in the width direction (extending along the direction in which the artery passes). Accordingly, the fluid bladder (and accordingly, the cuff including the fluid bladder) is easier to fit on the outer circumference of the above-described measurement site (with an outer diameter that is substantially constant). Accordingly, the pressure distribution on the measurement site is preferably flattened in the width direction.

With the fluid bladder of an embodiment, the number of segment bladders stacked in the thickness direction is odd.

The measurement site is substantially cylindrical rod-shaped, as with a wrist, for example, and has an outer diameter that gradually becomes smaller from the base end side through which the artery passes (the side close to the measurement subject's heart) to the terminal end side (the side far from the measurement subject's heart) in some cases. Here, with the fluid bladder of this embodiment, since the number of segment bladders stacked in the thickness direction is odd, in the state in which inflation is performed due to the fluid being supplied to the fluid bladder, the overall thickness of the multiple segment bladders changes in an inclined manner in the width direction (extending along the direction in which the artery passes). For example, on one end side in the width direction of the fluid bladder, the overall thickness of the multiple segment bladders is relatively thicker. In the central region in the width direction of the fluid bladder, the overall thickness of the multiple segment bladders is at an intermediate level. Also, on the other end side in the width direction of the fluid bladder, the overall thickness of the multiple segment bladders is relatively thinner. In this case, the cuff including the fluid bladder is attached to the measurement site in a state in which the one end side (the relatively thicker side) in the width direction of the fluid bladder corresponds to the terminal end side of the measurement site and the other end side (the relatively thinner side) in the width direction of the fluid bladder corresponds to the base end side of the measurement site. As a result, the fluid bladder (and accordingly, the cuff including the fluid bladder) is easily fit on the outer circumference of the above-described measurement site (with an outer diameter that gradually becomes smaller from the base end side to the terminal end side). Accordingly, the pressure distribution on the measurement site is preferably flattened in the width direction.

In another aspect, a fluid bladder manufacturing method according to one or more embodiments of the present invention is a fluid bladder manufacturing method for manufacturing the above-described fluid bladder, including:

preparing a plurality of substantially rectangular sheets with equal dimensions;

arranging an odd-numbered sheet in one direction and arranging an even-numbered sheet overlapping in a thickness direction, shifted by substantially a half-pitch with respect to the odd-numbered sheet in the one direction;

welding or adhering portions of half-sheets overlapping with each other of the odd-numbered sheet and the even-numbered sheet and thereby integrating them;

folding the odd-numbered sheet in half to a side opposite to that of the even-numbered sheet, welding or adhering edge portions on a side opposite to a folding location for folding in half, folding the even-numbered sheet in half to a side opposite to that of the odd-numbered sheet, and welding or adhering edge portions on a side opposite to a folding location for folding in half; and welding or adhering the edge portions in the lengthwise direction, which is orthogonal to the one direction, of two half-sheets that form the odd-numbered sheet, and welding or adhering the edge portions in the lengthwise direction of two half-sheets that form the even-numbered sheet.

Here, "one direction" corresponds to the width direction of the manufactured fluid bladder.

According to the fluid bladder manufacturing method according to one or more embodiments of the invention, the above-described fluid bladder can be easily manufactured.

In another aspect, a blood pressure measurement cuff according to one or more embodiments of the invention is a blood pressure measurement cuff including the above-described fluid bladder.

With the blood pressure cuff of this aspect, the above-described fluid bladder is included, and therefore the pressure distribution is flattened in the width direction extending along the artery that passes through the measurement site. Also, the stroke amount (swelling distance) in the thickness direction is increased, and the measurement site can be compressed.

In another aspect, a pressure measurement cuff according to one or more embodiments of the present invention includes:

a band-shaped body that includes a fluid bladder with an odd or even number of segment bladders stacked in the thickness direction; and a mark indicating an orientation in which the measurement site is to be inserted into the band-shaped body formed into a loop shape by being bent in the lengthwise direction, wherein the mark indicates, in the width direction, an orientation from the side at which the overall thickness of the plurality of segment bladders is relatively thin toward the side at which the overall thickness of the plurality of segment bladders is relatively thick when the fluid bladder is inflated due to fluid being supplied thereto.

As described above, the outer diameter of the measurement site gradually becomes smaller from the base end side to the terminal end side in some cases, for example. In this case, with the blood pressure measurement cuff of this aspect, it is desirable that the band-shaped body is attached to the measurement site in a state in which the one end side (the relatively thicker side) in the width direction of the fluid bladder corresponds to the terminal end side of the measurement site, and the other end side (the relatively thinner side) in the width direction of the fluid bladder corresponds to the base end side of the measurement site. Here, the cuff includes a mark indicating the orientation in which the measurement site is to be inserted into the band-shaped body that has been made into a loop shape by being bent in the lengthwise direction. The mark indicates, in the width direction, the orientation from the side at which the overall thickness of the multiple segment bladders is relatively thin (the other end side) toward the side at which the overall thickness of the multiple segment bladders is relatively thick (the one end side) when the fluid bladder is inflated due to the fluid being supplied thereto. Accordingly, when the cuff is attached to the measurement site, the measurement subject is prompted to insert the measurement site from the other end side (the relatively thin side) to the one end side (the relatively thick side) in the width direction, into the band-shaped belt that has been made into a loop shape by being bent in the lengthwise direction. Accordingly, the measurement subject is not mistaken about the orientation of attaching the cuff.

In another aspect, a blood pressure monitor according to one or more embodiments of the present invention includes the above-described blood pressure measurement cuff and a main body including an element for blood pressure measurement.

With the blood pressure monitor according to one or more embodiments of the present invention, it is possible to flatten the pressure distribution in the width direction due to the cuff, and the blood pressure measurement accuracy can be increased.

Advantageous Effects of the Invention

As is evident from the description above, with the fluid bladder and blood pressure measurement cuff according to one or more embodiments of the present invention, it is possible to flatten the pressure distribution in the width direction extending along the artery passing through the measurement site.

Also, with the fluid bladder manufacturing method according to one or more embodiments of the invention, such a fluid bladder can be easily manufactured.

Also, with the blood pressure monitor according to one or more embodiments of the present invention, it is possible to flatten the pressure distribution in the width direction due to the cuff, and the blood pressure measurement accuracy can be increased.

DESCRIPTION OF EMBODIMENTS

Hereinafter, embodiments of the present invention will be described in detail with reference to the drawings.

Figure 1:
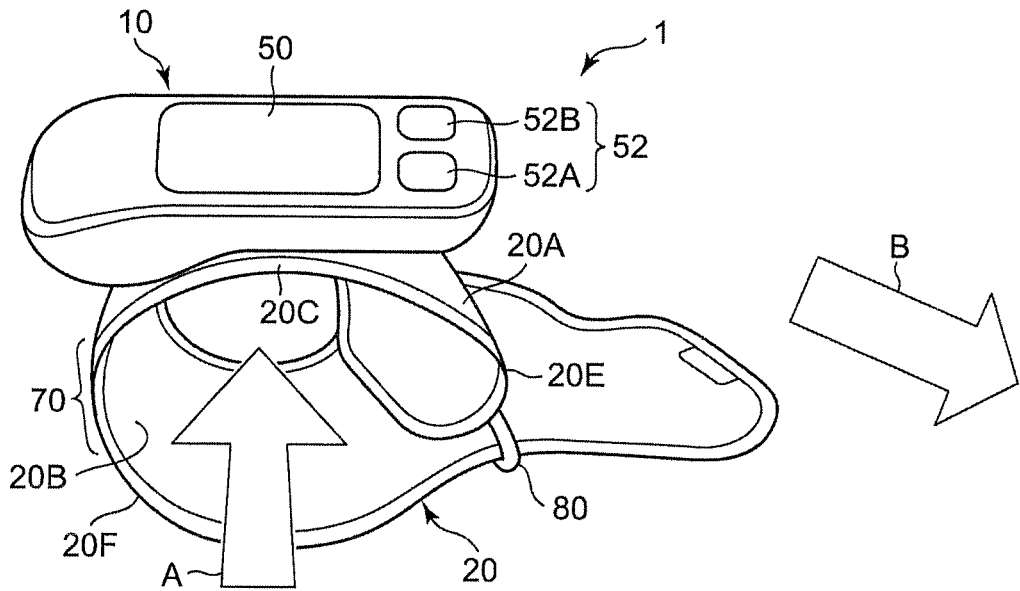
FIG. 1 is a perspective view showing an exterior of a blood pressure monitor having a blood pressure measurement cuff of an embodiment of the present invention.

FIG. 1 shows the exterior of a blood pressure monitor (indicated by reference numeral 1 overall) of an embodiment of the present invention. The blood pressure monitor 1 mainly includes a blood pressure measurement cuff 20 that is to be wrapped around a wrist 90 (e.g., see FIG. 5) serving as a measurement site, and a main body 10 that is integrally attached along the outer circumferential surface of the cuff 20 and has a built-in element for blood pressure measurement. A later-described display device 50 and an operation unit 52 are arranged on the outer surface on the side of the main body 10 opposite to the cuff 20.

Figure 5:
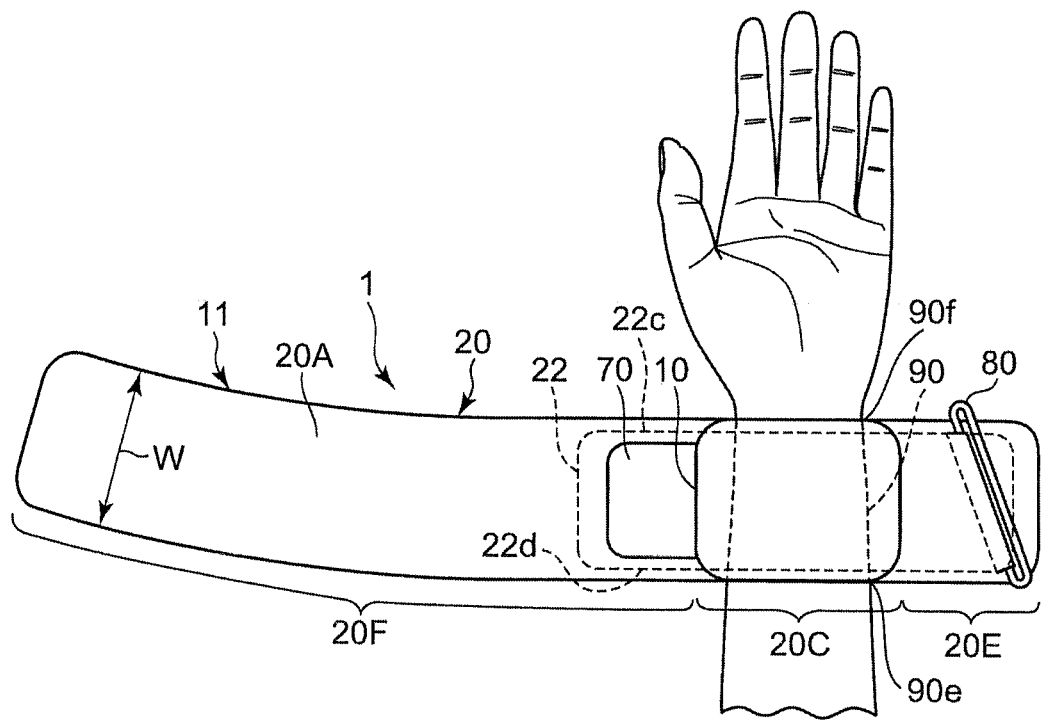
FIG. 5 is a diagram schematically showing a planar layout in a view of the blood pressure monitor from the side on which the main body is provided with the cuff expanded.

FIG. 5 schematically shows a planar layout of a view of the blood pressure monitor 1 from a side (corresponds to the outer circumferential side in FIG. 1) on which the main body 10 is provided, in a state in which the cuff 20 is expanded. Also, FIG. 6 schematically shows a planar layout of a view of the blood pressure monitor 1 from a side (corresponds to the inner circumferential side in FIG. 1) opposite to that shown in FIG. 5, in a state in which the cuff 20 is expanded.

Figure 6:
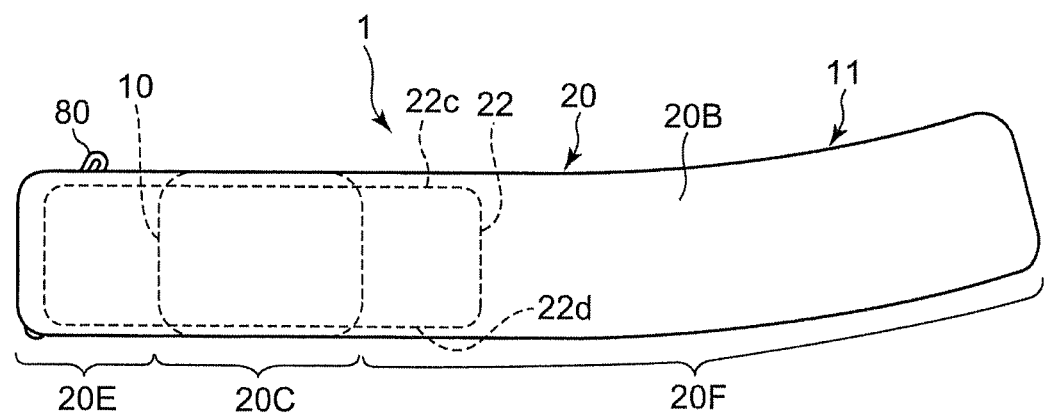
FIG. 6 is a diagram showing a planar layout in a view of the blood pressure monitor from a side opposite to that of FIG. 5 with the cuff expanded.

As can be understood from FIGS. 5 and 6, the cuff 20 is formed as a bladder-shaped band-shaped body 11 by sewing an outer cloth 20A and an inner cloth 20B along their circumferential edges. In order to make it easier to compress the measurement site, the inner cloth 20B has a large elasticity, and the outer cloth 20A is set to be substantially non-elastic (or to have a smaller elasticity compared to the inner cloth 20B).

In the lengthwise direction (corresponds to the circumferential direction in FIG. 1) of the cuff 20, the cuff 20 includes a second portion 20C that extends along the main body 10, a first portion 20E that extends from the second portion 20C to one side (the right side in FIG. 5), and a third portion 20F that extends from the second portion 20C to the other side (the left side in FIG. 5). For example, the dimension in the lengthwise direction of the cuff 20 is set within a range of 300 mm to 400 mm, and the dimension W in the width direction is set within a range of 30 mm to 60 mm.

The third portion 20F curves so as to bulge downward in FIGS. 5 and 6. The orientation of the curve is obtained by envisioning that the cuff 20 is attached by being wrapped around the wrist 90 such that the hand side (thin side) 90f, which is the terminal end side of the wrist 90, is located above and the elbow side 90e, which is the base end side of the wrist 90, is located below in FIGS. 5 and 6.

A ring 80 having a substantially oval shape is attached to the outer circumferential surface of the first portion 20E. The lengthwise direction of the ring 80 intersects the lengthwise direction of the cuff 20. The dimension in the lengthwise direction of the ring 80 is set to be slightly larger than the width direction dimension W of the cuff 20 so that the cuff 20 (i.e., the third portion 20F) can be easily passed therethrough.

A surface fastener 70 is attached to the surface of a nearby portion near the main body 10 of the third portion 20F of the cuff 20. In this example, the surface fastener 70 has many small hooks (not shown) on its surface. The outer circumferential surface of the portion other than the nearby portion (the surface fastener 70) of the third portion 20F has many small loops (not shown) that engage with the hooks.

An air bladder 22 serving as the fluid bladder for compressing the wrist 90 is contained in the cuff 20, spanning from the first portion 20E to the third portion 20F.

Figure 7:
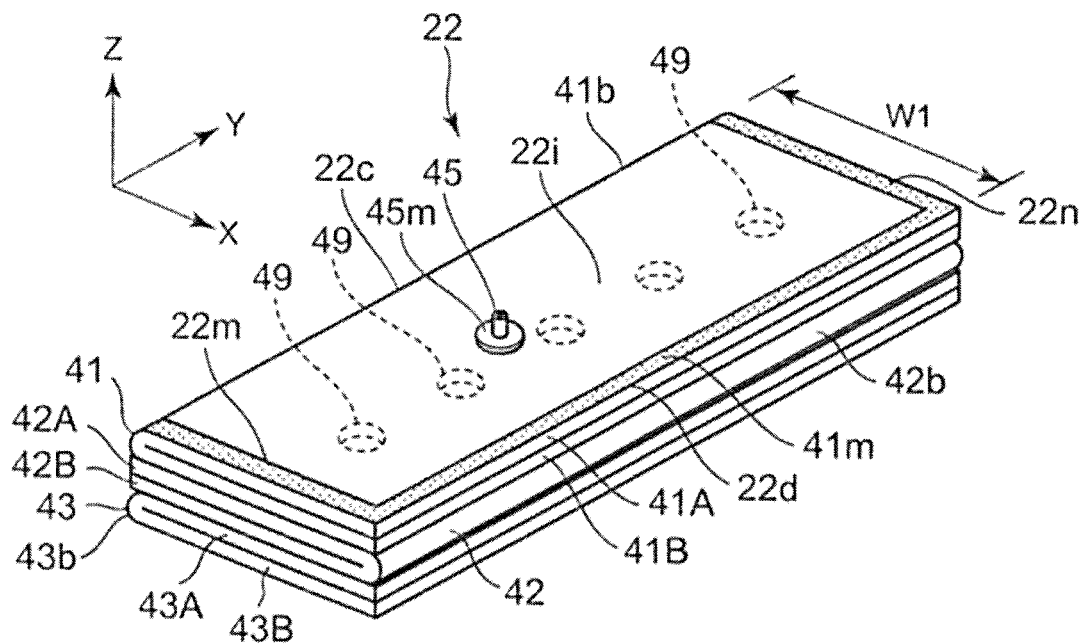
FIG. 7 is a perspective view showing an exterior of an air bladder serving as a fluid bladder contained in the cuff.

FIG. 7 shows a perspective view of the exterior of the air bladder 22. The width direction (X direction) of the air bladder 22 corresponds to the width direction of the cuff 20, or in other words, the direction extending along the artery passing through the wrist 90. The lengthwise direction (Y direction) and thickness direction (Z direction) of the air bladder 22 correspond respectively to the lengthwise direction and the thickness direction of the cuff 20. Note that in order to facilitate understanding, the orthogonal coordinate system XYZ is shown as well in FIG. 7 (the same follows for later-described FIGS. 8A, 8B, 9A, 9B, 9C, and 10 to 12).

The air bladder 22 includes multiple (in this example, three) integrated segment bladders 41, 42, and 43 with the same dimensions, which are stacked sequentially in the thickness direction Z, which is orthogonal to the wrist 90 serving as the measurement site. The segment bladder 41 is arranged on the side located far from the wrist 90 (corresponds to the outer circumferential side in FIG. 1), whereas the segment bladder 43 is arranged on the side located near the wrist 90 (corresponds to the inner circumferential side in FIG. 1). The segment bladders 41, 42, and 43 are each obtained by folding a sheet in half in the width direction X, the edge portions on the sides opposite to the folding locations 41b, 42b, and 43b for folding in half are welded, and the edge portions in the lengthwise direction Y are welded. In particular, in this example, the edge portions in the lengthwise direction Y of the segment bladders 41, 42, and 43 are collectively welded in the thickness direction Z (the welding location of the edge portion on the −Y side and the welding location of the edge portion on the +Y side are respectively denoted by reference numerals 22m and 22n). The folding locations 41b, 42b, and 43b of the segment bladders 41, 42, and 43 are arranged alternatingly on opposite sides in the width direction X. In this example, the folding locations 41b and 43b of the odd-numbered segment bladders 41 and 43 are arranged on one end side (−X side) 22c. The folding location 42b of the even-numbered segment bladder 42 is arranged on the other end side (+X side) 22d.

Through holes 49 and 49' (see FIG. 8A) that allow air to flow between the segment bladders 41 and 42 and between the segment bladders 42 and 43 are provided between the mutually-adjacent segment bladders 41 and 42 and between the mutually-adjacent segment bladders 42 and 43.

Also, an approximately circular tube-shaped nipple for supplying air from an external supplying source (a later-described pump 32) and discharging the air from inside of the air bladder 22 is attached to the half-sheet 41A of the segment bladder 41 (the portion corresponding to the inner diameter of the nipple 45 of the half-sheet 41A is formed so as to penetrate therethrough; this is simply denoted using the expression "the nipple 45 is attached" as appropriate). Note that "half-sheet" denotes sheets 41A, 41B, 42A, 42B, 43A, and 43B, which are substantially halves of sheets 41, 42, and 43 (for the sake of simplicity, the segment bladders are denoted by the same reference numerals thereas) that are segmented (or are to be segmented) by the folding locations 41$b$, 42$b$, and 43$b$.

For example, the overall dimension in the lengthwise direction Y of the air bladder 22 including the segment bladders 41, 42, and 43 is set to be approximately half of the dimension in the lengthwise direction Y of the cuff 20. Also, the dimension W1 in the width direction X of the air bladder 22 is set to be approximately 5 mm smaller than the dimension W in the width dimension of the cuff 20. The material of the segment bladders (sheets) 41, 42, and 43 is polyurethane resin in this example.

Figure 9A:
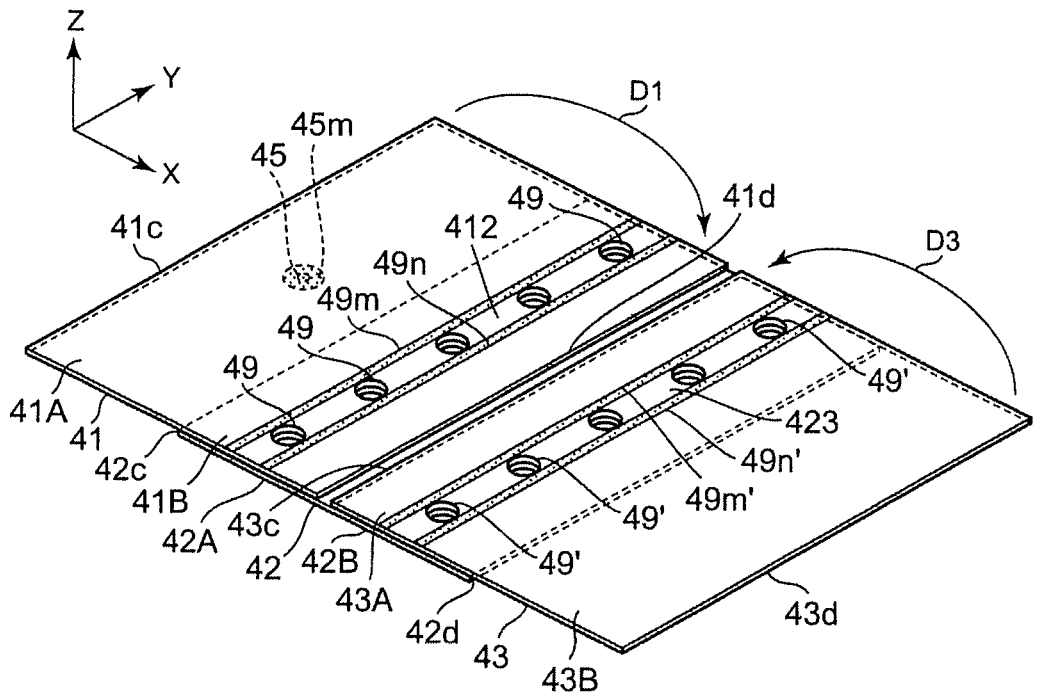
FIG. 9A is a diagram illustrating a manufacturing step of manufacturing the air bladder shown in FIG. 7.
Figure 9B:
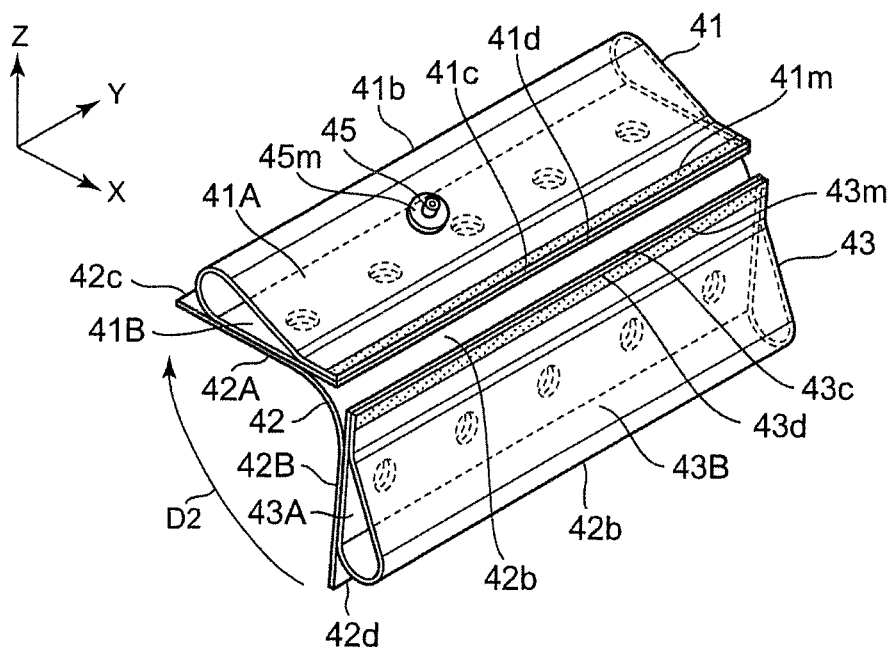
FIG. 9B is a diagram illustrating a manufacturing step of manufacturing the air bladder shown in FIG. 7.

The air bladder 22 is produced as follows, for example.

i) First, as shown in FIG. 9A, multiple (in this example, three) sheets 41, 42, and 43 that are substantially rectangular and have equal dimensions are prepared (note that in order to facilitate understanding, the same reference numerals are used for the segment bladders and the sheets for forming them). An approximately circular tube-shaped nipple 45 is attached in advance through welding to the approximate center (the lower surface in FIG. 9A) of the half-sheet 41A on the −X side of the sheet 41 (the welding location around the nipple 45 is indicated by reference numeral 45$m$).

ii) Next, the odd-numbered sheets 41 and 43 are arranged in alignment in one direction with hardly any gap provided between the sheets 41 and 43 (in this example, for the sake of simplicity, the one direction is described as matching the X direction, but can be any direction in the production stage). In addition, the even-numbered sheet 42 is shifted in the +X direction by substantially a half-pitch with respect to the odd-numbered sheets 41 and 43 in the X direction, and is arranged overlapping therewith (adjacent thereto) in the thickness direction Z. In this example, the sheet 42 is arranged overlapping on the lower side (−Z side), spanning between the sheets 41 and 43.

iii) Next, the portions of the half-sheets that overlap with each other in the thickness direction Z of the odd-numbered sheets 41 and 43 and the even-numbered sheet 42 are welded and integrated. In this example, portions 49$m$ and 49$n$ of the half-sheet 41B on the +X side of the sheet 41 and the half-sheet 42A on the −X side of the sheet 42 that extend in two stripe shapes in the Y direction at the approximate center in the X direction are welded and integrated. In addition, portions 49$m$' and 49$n$' of the half-sheet 42B on the +X side of the sheet 42 and the half-sheet 43A on the −X side of the sheet 43 that extend in two stripe shapes in the Y direction at the approximate center in the X direction are welded and integrated.

iv) Next, in this example, five through holes 49, 49, . . . are formed at equal intervals in the Y direction on the inner region (excluding the edge portion on the −Y side and the edge portion on the +Y side) 412 between the portions 49$m$ and 49$n$ of the half-sheet 42B on the +X side of the sheet 42 and the half-sheet 43A on the −X side of the sheet 43 that extend in stripe shapes. In addition, five through holes 49', 49', . . . are formed at equal intervals in the Y direction on the inner region (excluding the edge portion on the −Y side and the edge portion on the +Y side) 423 between the portions 49$m$' and 49$n$' of the half-sheet 42B on the +X side of the sheet 42 and the half-sheet 43A on the −X side of the sheet 43 that extend in stripe shapes.

v) Next, as indicated by arrows D1 and D3 in FIG. 9A, the odd-numbered sheets 41 and 43 are folded in half toward the side opposite to that of the even-numbered sheet 42. Then, as shown in FIG. 9B, the edge portions 41$c$ and 41$d$ on the side opposite to the folding location 41$b$ for folding in half of the sheet 41 are welded together, and the edge portions 43$c$ and 43$d$ on the side opposite to the folding location 43$b$ for folding in half of the sheet 43 are welded together (the welding locations are denoted by reference numerals 41$m$ and 43$m$).

vi) Also, as indicated by the arrow D2 in FIG. 9B, the even-numbered sheet 42 is folded in half to the side opposite to that of the odd-numbered sheets 41 and 43. Then, as shown in FIG. 9C, the edge portions 42$c$ and 42$d$ on the side opposite to the folding location 42$b$ for folding in half of the sheet 42 are welded together (the welding location is denoted by reference numeral 42$m$).

Figure 9C:
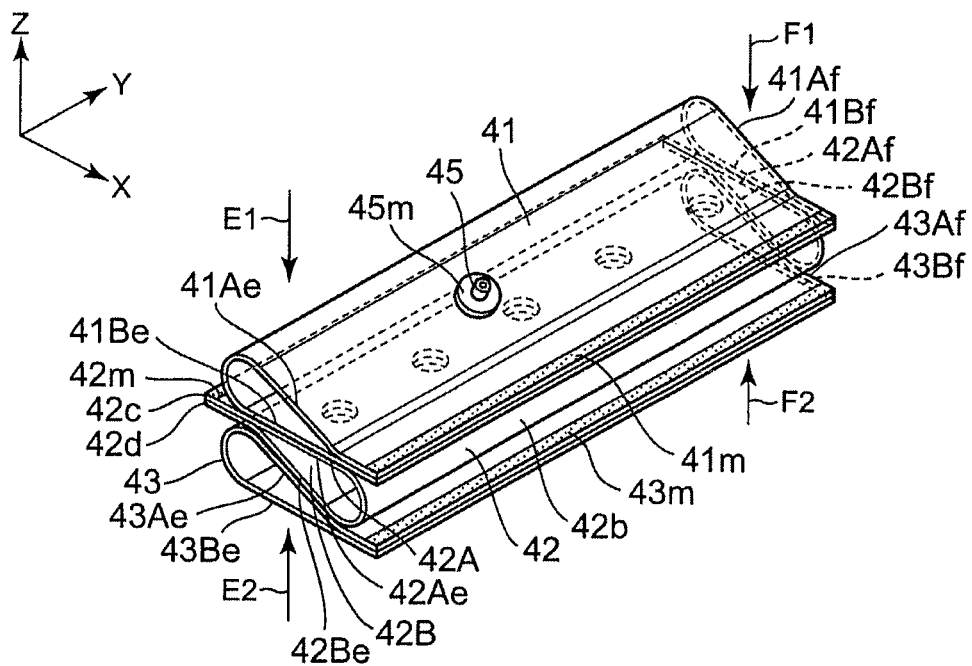
FIG. 9C is a diagram illustrating a manufacturing step of manufacturing the air bladder shown in FIG. 7.

Note that the step vi) may be performed before the step v). Also, the step v) and the step vi) may be performed in parallel.

vii) Next, as indicated by arrows E1 and E2 in FIG. 9C, edge portions 41Ae and 41Be on the −Y side of the half-sheets 41A and 41B that form the sheet 41, the edge portions 42Ae and 42Be on the −Y side of the half-sheets 42A and 42B that form the sheet 42, and the edge portions 43Ae and 43Be on the −Y side of the half-sheets 43A and 43B that form the sheet 43 are collectively welded in the thickness direction Z. In addition, as indicated by the arrows F1 and F2, the edge portions 41Af and 41Bf on the +Y side of the half-sheets 41A and 41B forming the sheet 41, the edge portions 42Af and 42Bf on the +Y side of the half-sheets 42A and 42B forming the sheet 42, and the edge portions 43Af and 43Bf on the +Y side of the half-sheets 43A and 43B forming the sheet 43 are collectively welded in the thickness direction Z.

Accordingly, the air bladder 22 shown in FIG. 7 is obtained (as described above, in FIG. 7, the welding location of the edge portions on the −Y side and the welding location of the edge portions on the +Y side are respectively denoted by reference numerals 22$m$ and 22$n$).

With the obtained air bladder 22, the half-sheets 41B and 42A that are adjacent to each other are welded such that the five through holes 49 are surrounded overall by the welded stripe-shaped portions 49$m$ and 49$n$ (see FIG. 9A) and the welding locations 22$m$ and 22$n$. Also, the half-sheets 42B and 43A that are adjacent to each other are welded such that the five through holes 49' are surrounded overall by the welded stripe-shaped portions 49$m$' and 49$n$' and the welding locations 22$m$ and 22$n$. Accordingly, leakage of air from the through holes 49 through the gap between the half-sheets 41B and 42A that are adjacent to each other is prevented. Also, leakage of air from the through holes 49' through the gap between the half-sheets 42B and 43A that are adjacent to each other is prevented.

Figure 8A:
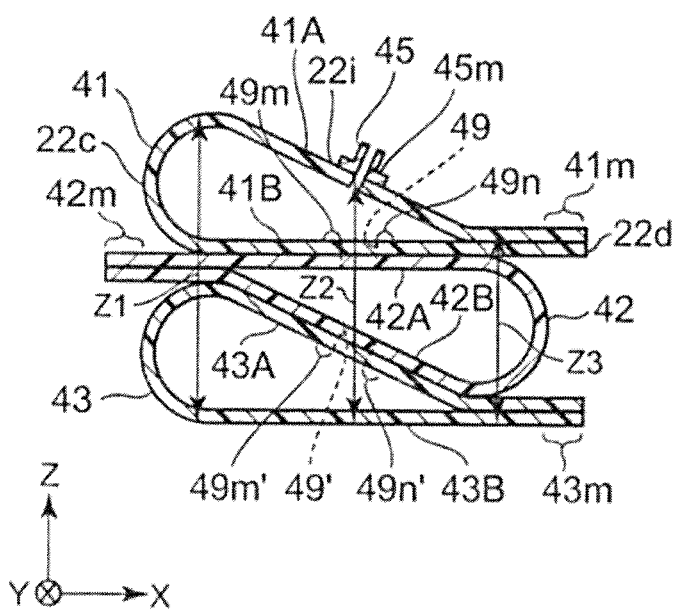
FIGS. 8A and 8B are diagrams showing cross-sections taken by cutting the air bladder in a width direction X and a lengthwise direction Y respectively, in a state in which a small amount of air has been supplied to the air bladder shown in FIG. 7.
Figure 8B:
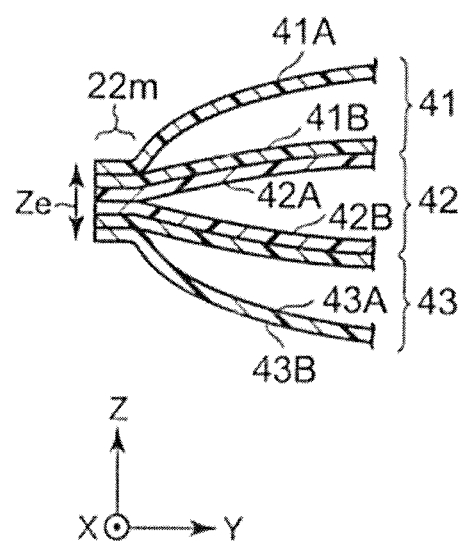

FIG. 8A shows a cross-section taken by cutting the air bladder 22 along the width direction X in a state in which a small amount of air serving as the fluid has been supplied (introduced) to the air bladder 22 from the outside through the nipple 45 so as to inflate the air bladder 22. Also, FIG. 8B shows a cross-section near the edge portion on the −Y side, which is taken by cutting the air bladder 22 along the lengthwise direction Y in the same state as in FIG. 8A. As shown in the drawings, the segment bladders 41 and 42 that are adjacent to each other and the segment bladders 42 and 43 that are adjacent to each other are in communication through the through holes 49 and 49' and thus air can flow through, and therefore the three segment bladders 41, 42, and 43 are inflated to the same pressure and swell. Note that conversely, the air can be discharged from all of the multiple segment bladders 41, 42, and 43 through the nipple 45.

With the air bladder 22, the three segment bladders 41, 42, and 43 are stacked in the thickness direction Z, and therefore, similarly to the air bladder of the conventional example, the stroke amount in the thickness direction Z (swelling distance) is increased in comparison to the case of being simply composed of one fluid bladder and the wrist 90 can be compressed.

Also, as shown in FIG. 8A, when inflated due to air being supplied thereto, the segment bladders 41, 42, and 43 have so-called teardrop-shaped cross-sections according to the above-described configuration. In this example, the segment bladders 41 and 43 have teardrop-shaped cross-sections in which the +X side tapers to a point and the −X side curves in a circular arc shape. The segment bladder 42 has a cross-section in which the −X side tapers to a point and the +X side curves in a circular arc shape. In other words, with the air bladder 22, in the region on the one end side (−X side) 22c in the width direction X, the relatively thick portions of the segment bladders 41 and 43 and the relatively thin portion of the segment bladder 42 adjacent thereto are stacked alternatingly in the thickness direction Z. As a result, in the region of the one end side 22c, the overall thickness Z1 of the segment bladders 41, 42, and 43 is made uniform. In the region of the center 22i in the width direction X of the air bladder 22, the portions with intermediate-level thicknesses of the segment bladders 41, 42, and 43 are stacked. As a result, in the region of the center 22i, the overall thickness Z2 of the segment bladders 41, 42, and 43 is made uniform. Also, in the region on the other end side (+X side) 22d in the width direction X of the fluid bladder 22, the relatively thin portions of the segment bladders 41 and 43 and the relatively thick portion of the segment bladder 42 adjacent thereto are stacked alternatingly in the thickness direction Z. As a result, in the air bladder 22, in the region of the other end side 22d, the overall thickness Z3 of the segment bladders 41, 42, and 43 is made uniform.

Also, in this example, the number of segment bladders 41, 42, and 43 stacked in the thickness direction Z is odd (three), and therefore the overall thicknesses Z1, Z2, and Z3 of the segment bladders 41, 42, and 43 change in an inclined manner. In this example, in the region of the one end side (−X side) 22c in the width direction X of the air bladder 22, the overall thickness Z1 of the segment bladders 41, 42, and 43 is relatively thick. In the region of the center 22i in the width direction X of the air bladder 22, the overall thickness Z2 of the segment bladders 41, 42, and 43 is at an intermediate level. Also, in the region of the other end side (+X side) 22d in the width direction X of the air bladder 22, the overall thickness Z3 of the segment bladders 41, 42, and 43 is relatively thin.

Note that as shown in FIG. 8B, the edge portions on the −Y side (the same follows for the edge portions on the + side as well) in the lengthwise direction Y of the air bladder 22 are collectively welded, and therefore the thickness Ze is relatively thin.

The air bladder 22 is contained in the cuff 20 such that the nipple 45 attached to the sheet 41 protrudes through the outer cloth 20A. Also, in this example, as shown in FIGS. 5 and 6, the air bladder 22 is contained in the cuff 20 in an orientation in which the one end side 22c that is relatively thick when inflated is located above and the other end side 22d that is relatively thin is located below. The orientation of the air bladder 22 corresponds to the fact that the air bladder 22 is attached by being wrapped around the wrist 90 such that the hand side (thin side) 90f of the wrist 90 is located above and the elbow side (thick side) 90e of the wrist 90 is located below (this will be described in detail later).

Figure 3:
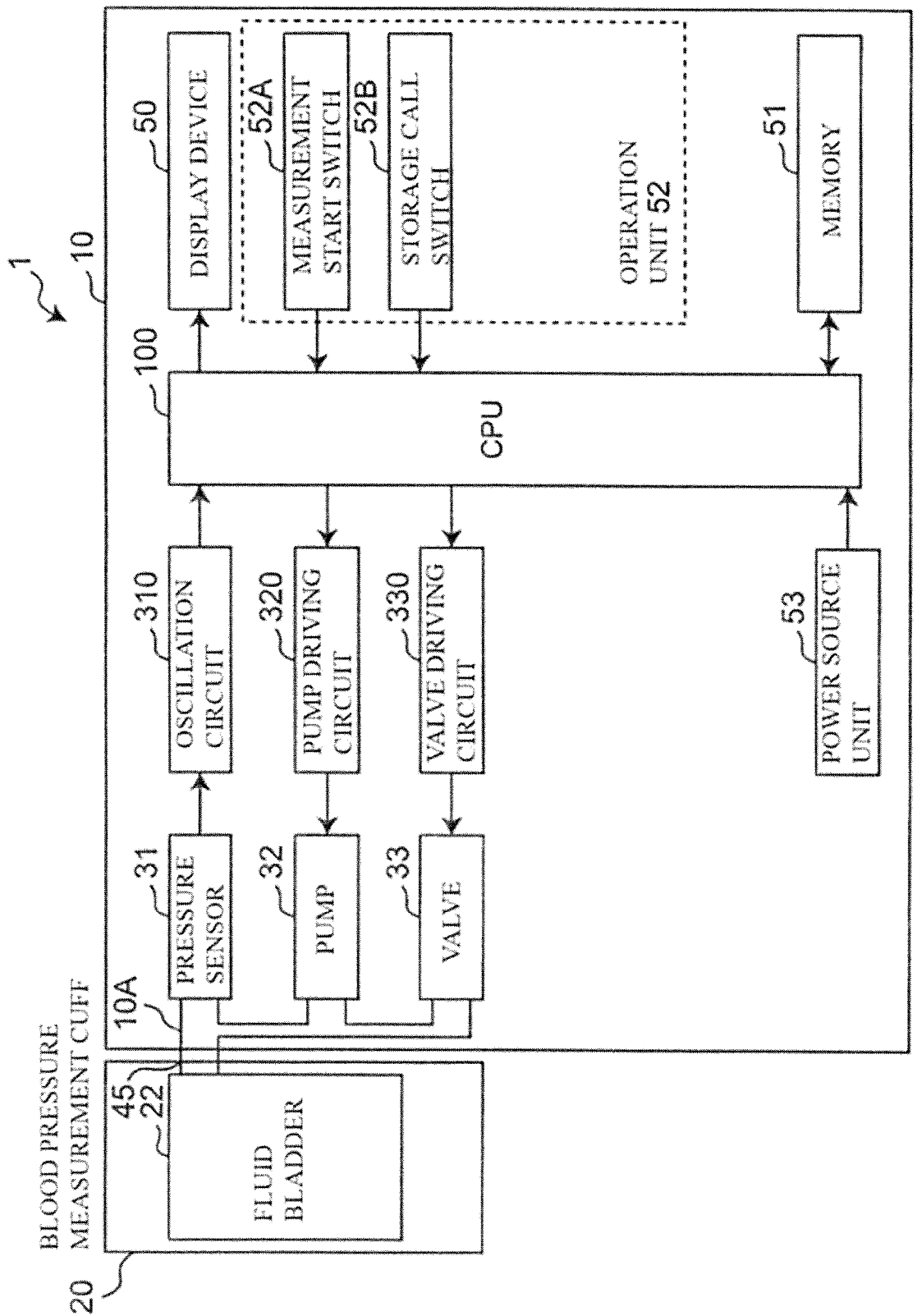
FIG. 3 is a diagram showing a schematic block configuration of the blood pressure monitor.

When the main body 10 and the cuff 20 are coupled, as shown in FIG. 3, the air tube 10A of the main body 10 is air-tightly fit into the nipple 45 of the air bladder 22. The main body 10 and the cuff 20 are coupled together by a coupling means (not shown) (an engaging protrusion and a depression with which the engaging protrusion engages, adhesive, or the like). In this manner, the main body 10 and the cuff 20 are integrated.

FIG. 3 shows a schematic block configuration of the cuff 20 and the main body 10 of the blood pressure monitor 1. The blood pressure monitor 1 includes a CPU (Central Processing Unit) 100 serving as a control unit, a display device 50, a memory 51 serving as a storage unit, an operation unit 52, a power source unit 53, a pump 32, a valve 33, and a pressure sensor 31, which are mounted in the main body 10. Also, the main body 10 includes an oscillation circuit 310 that converts output from the pressure sensor 31 into a frequency, a pump driving circuit 320 that drives the pump 32, and a valve driving circuit 330 that drives the valve 33, which are mounted in the main body 10.

The display device 50 includes a display, an indicator, and the like and displays predetermined information such as blood pressure measurement results according to a control signal from the CPU 100.

The operation unit 52 includes a measurement start switch 52A for receiving an instruction to start blood pressure measurement, and a storage call switch 52B for calling blood pressure measurement results stored in the memory. These switches 52A and 52B input operation signals corresponding to instructions given by a user to the CPU 100.

The memory 51 stores data of programs for controlling the blood pressure monitor 1, data to be used to control the blood pressure monitor 1, setting data for setting various functions of the blood pressure monitor 1, data of blood pressure value measurement results, and the like. Also, the memory 51 is used as a work memory and the like for when a program is executed.

The CPU 100 performs control for driving the pump 32 and the valve 33 in response to an operation signal from the operation unit 52, according to a program for controlling the blood pressure monitor 1 stored in the memory 51. Also, based on the signal from the pressure sensor 31, the CPU 100 calculates the blood pressure value and controls the display device 50 and the memory 51.

The power source unit 53 supplies power to the units, namely the CPU 100, the pressure sensor 31, the pump 32, the valve 33, the display device 50, the memory 51, the oscillation circuit 310, the pump driving circuit 320, and the valve driving circuit 330.

The pump 32, the valve 33, and the pressure sensor 31 are connected to the air bladder 22 contained in the cuff 20 via the common air tube 10A. The pump 32 supplies air to the air bladder 22 through the air tube 10A in order to increase the air pressure (cuff pressure) in the air bladder 22 contained in the cuff 20. The valve 33 is a solenoid valve that is controlled so as to open and close through application of an electric current, and is used to control the cuff pressure by discharging the air in the air bladder 22 through the air tube 10A or sealing the air in the air bladder 22. The pump driving circuit 320 drives the pump 32 based on a control signal applied from the CPU 100. The valve driving circuit 330 opens and closes the valve 33 based on a control signal applied from the CPU 100.

In this example, the pressure sensor 31 is a piezoresistance pressure sensor and detects the pressure of the cuff 20 (the air bladder 22) through the air tube 10A and outputs it as a cuff pressure signal (indicated by reference numeral Pc) in a time series. The oscillation circuit 310 oscillates based on an electrical signal value obtained based on changes in electrical resistance due to the piezoresistance effect from the pressure sensor 31 and outputs a frequency signal having a frequency corresponding to the electrical signal value of the pressure sensor 31 to the CPU 100.

Figure 2:
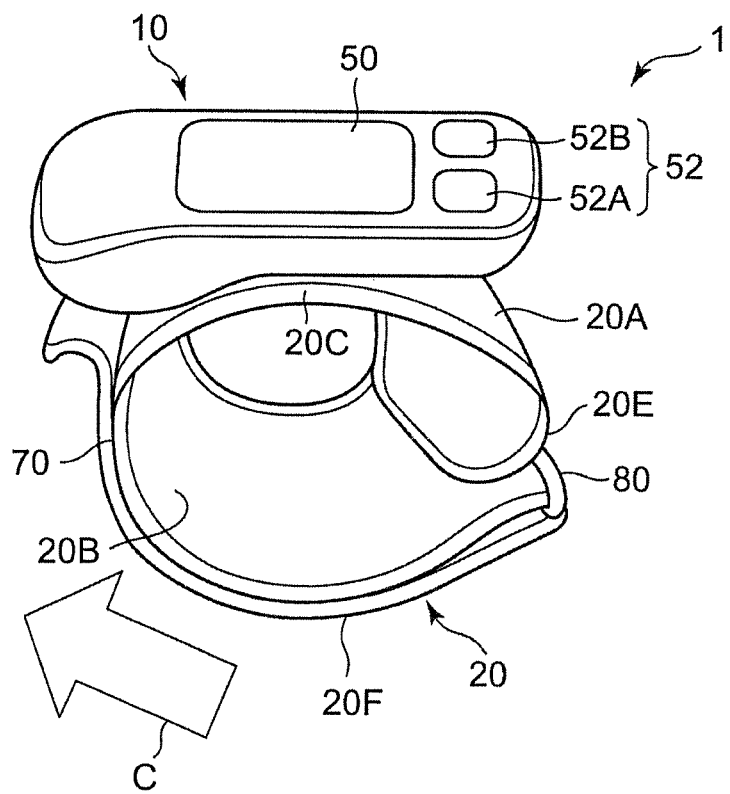
FIG. 2 is a perspective view showing a state at a time when the blood pressure monitor is attached to a measurement site (not shown).

When the blood pressure monitor 1 (cuff 20) is attached to the wrist 90 serving as the measurement site, as shown in FIG. 1, the cuff 20 (band-shaped body 11) is bent in the lengthwise direction and the third portion 20F of the cuff 20 is passed through the ring 80 to form a loop shape. The wrist 90 is inserted in the cuff 20 as indicated by arrow A in FIG. 1, with the palm facing upward. Accordingly, the second portion 20C of the cuff 20 is placed on the wrist 90 together with the main body 10. Next, the portion of the third portion 20F of the cuff 20 that is far from the main body 10 is passed through the ring 80, is pulled downward and to the right in FIG. 1 as indicated by arrow B, and is folded over as indicated by arrow C in FIG. 2. Then, the folded-over portion is fixed by being pressed to the surface fastener 70.

Figure 13:
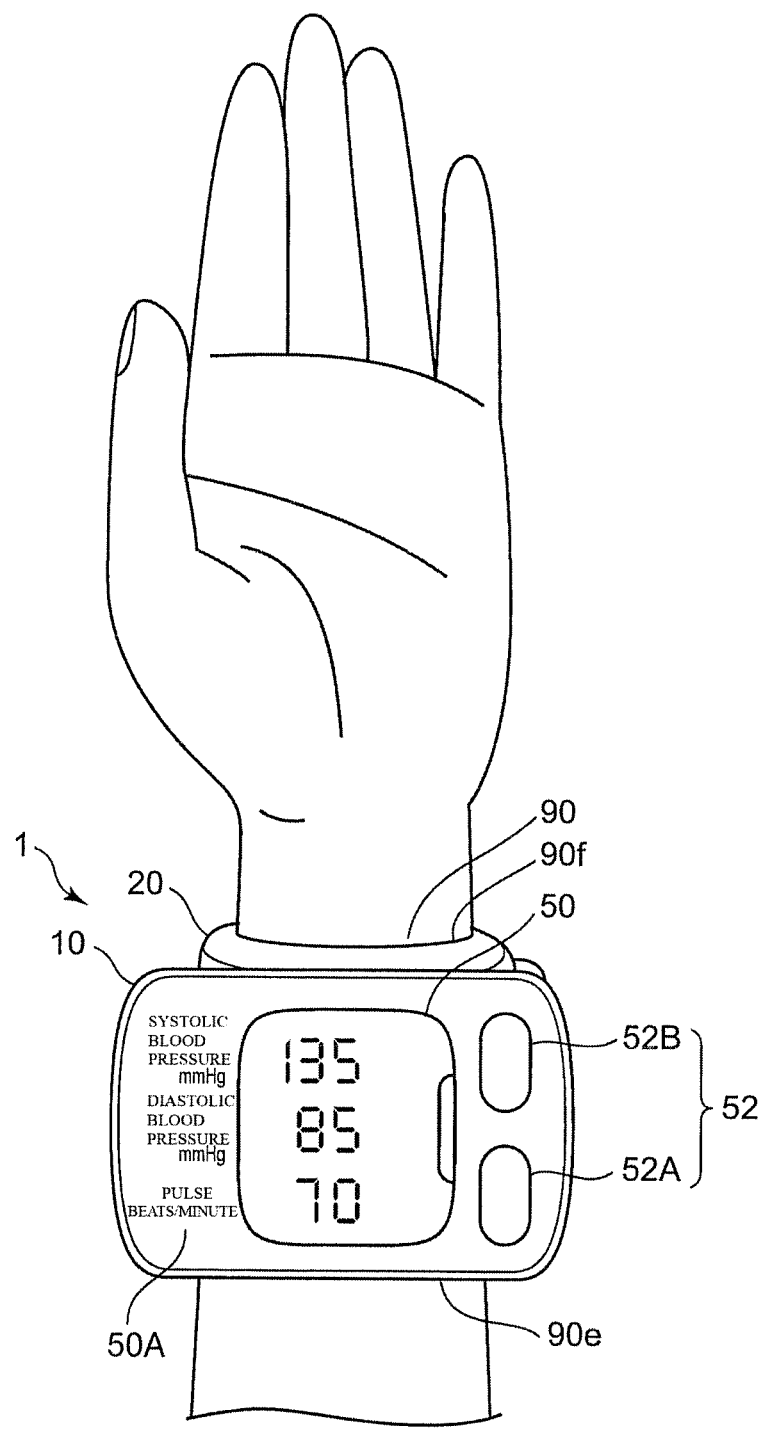
FIG. 13 is a diagram showing a measurement subject's view of a display device of a blood pressure monitor main body in a state in which the blood pressure monitor (cuff) shown in FIG. 1 is attached to a wrist.

FIG. 13 shows a view taken by the measurement subject of the display device 50 of the blood pressure monitor main body 10 in its natural orientation, in a state in which the blood pressure monitor 1 (cuff 20) is attached to the wrist 90. The outer surface of the main body 10 is provided with a printed display 50A that reads "systolic blood pressure mmHg", "diastolic blood pressure mmHg", and "pulse beats/minute" in the stated order starting from the top along the left side of the display device 50. When the measured values are obtained due to blood pressure measurement being performed, the display device 50 displays the measured value (in this example, 135 mmHg) of the systolic blood pressure, the measured value (in this example, 85 mmHg) of the diastolic blood pressure, and the measured value (in this example, 70 beats per minute) of the pulse on the right side of the print display 50A. These measured values (displayed content) are displayed upright as viewed by the measurement subject. Accordingly, the measurement subject can easily check the measured values. Conversely, the print display 50A functions as a mark indicating the orientation in which the wrist 90 is to be inserted into the cuff 20. Due to the print display 50A, the measurement subject is prompted to insert his or her wrist 90 into the cuff 20 in an orientation in which the display of the display device 50 can be viewed upright. Accordingly, the measurement subject is not mistaken about the orientation of attaching the cuff 20.

Figure 14:
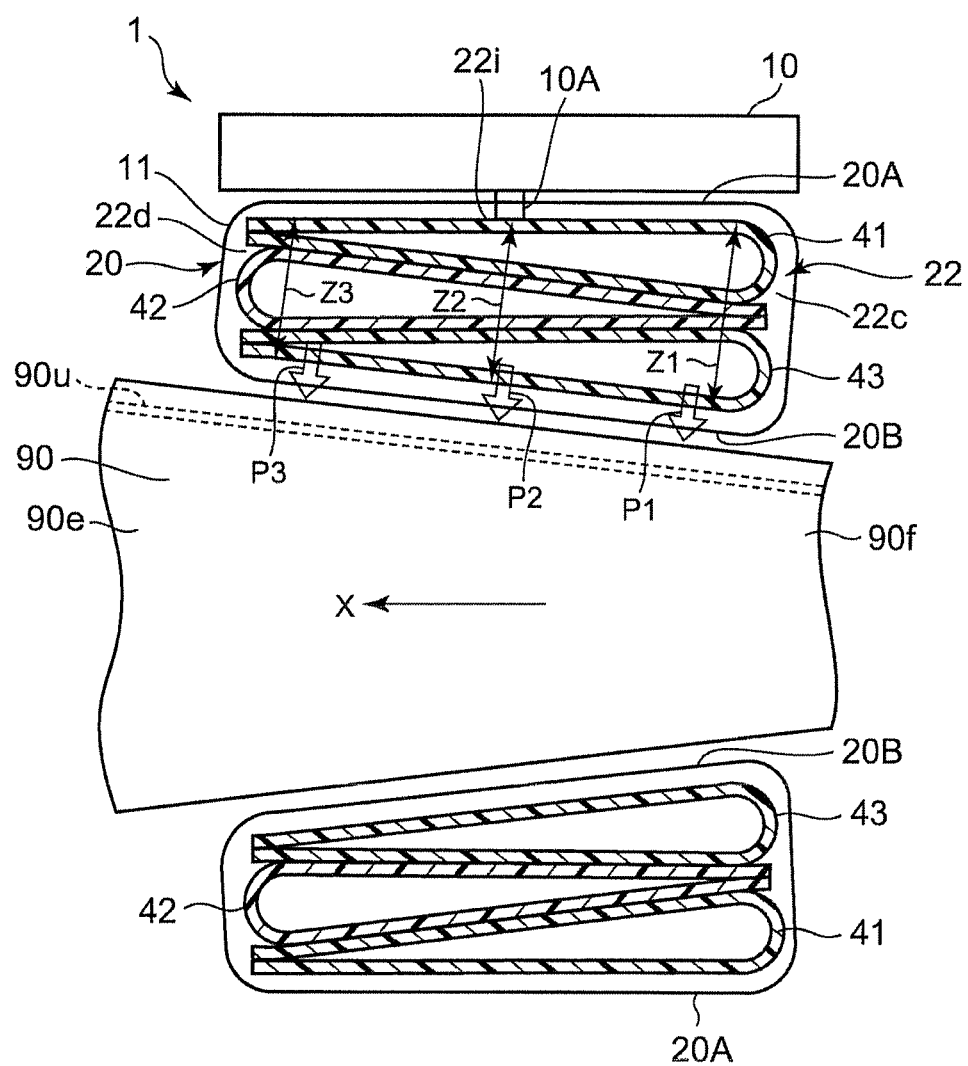
FIG. 14 is a diagram showing a cross-section taken by cutting along an artery passing through a wrist, or in other words, a cross-section taken along the width direction X of the cuff in a state in which the cuff (blood pressure monitor) containing the air bladder shown in FIG. 7 is attached to the wrist.

FIG. 14 shows a cross-section in the width direction X extending along an artery 90u that passes through the wrist 90, in a state in which the cuff 20 is attached to the wrist 90. In the state in which the cuff 20 is attached to the wrist 90 in accordance with the orientation indicated by the print display 50A as described above (FIG. 13), as shown in FIG. 14, the one end side 22c that is relatively thick during inflation of the air bladder 22 corresponds to the hand side 90f of the wrist 90 and the other end side 22d that is relatively thin during inflation of the air bladder 22 corresponds to the elbow side 90e of the wrist 90. As a result, the cuff 20 containing the air bladder 22 more easily fits on the outer circumference of the above-described wrist 90 (the outer diameter gradually decreases from the elbow side 90e to the hand side 90f). Accordingly, in the width direction X, the pressure distribution on the wrist 90 is preferably flattened. For example, the pressure P1 at the region of the one end side (−X side) 22c in the width direction X of the air bladder 22, the pressure P2 at the region in the center 22i in the width direction C, and the pressure P3 at the region of the other end side (+X side) 22d in the width direction X can be made approximately equal, and the pressure distribution can be flattened. As a result, it is possible to prevent noise from occurring in the cuff pressure signal and the blood pressure value measurement accuracy can be increased.

Figure 17:
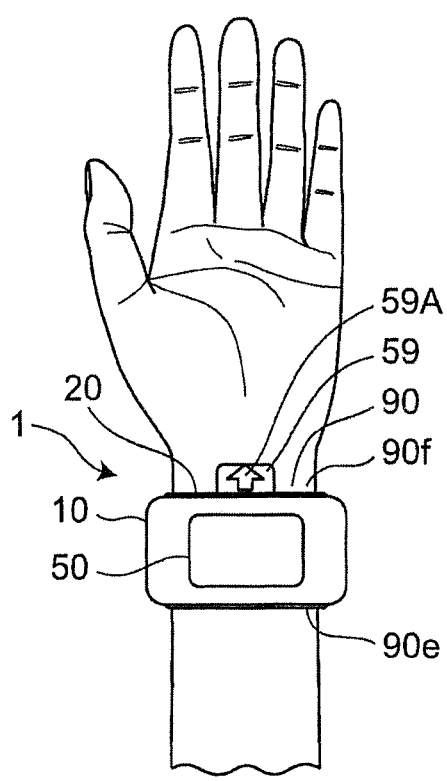
FIG. 17 is a diagram illustrating a mark indicating an orientation in which the wrist is to be inserted into the cuff.

Note that the mark indicating the orientation in which the wrist 90 is to be inserted into the cuff 20 is not limited to the above-described printed display 50A. Instead of, or in addition to this, a tab 59 shown in FIG. 17 for example may be provided. The tab 59 is attached so as to protrude outward in the width direction on the cuff 20. An arrow 59A indicating the orientation in which the wrist 90 is to be inserted into the cuff 20 (the orientation from bottom to top in FIG. 17) is indicated on the tab 59. When the measurement subject inserts the wrist 90 into the cuff 20 in accordance with the orientation indicated by the arrow 59A, as shown in FIG. 14, the one end side 22c that is relatively thick during inflation of the air bladder 22 corresponds to the hand side 90f of the wrist 90 and the other end side 22d that is relatively thin during inflation of the air bladder 22 corresponds to the elbow side 90e of the wrist 90. Accordingly, the measurement subject is not mistaken about the orientation of attaching the cuff 20.

Figure 4:
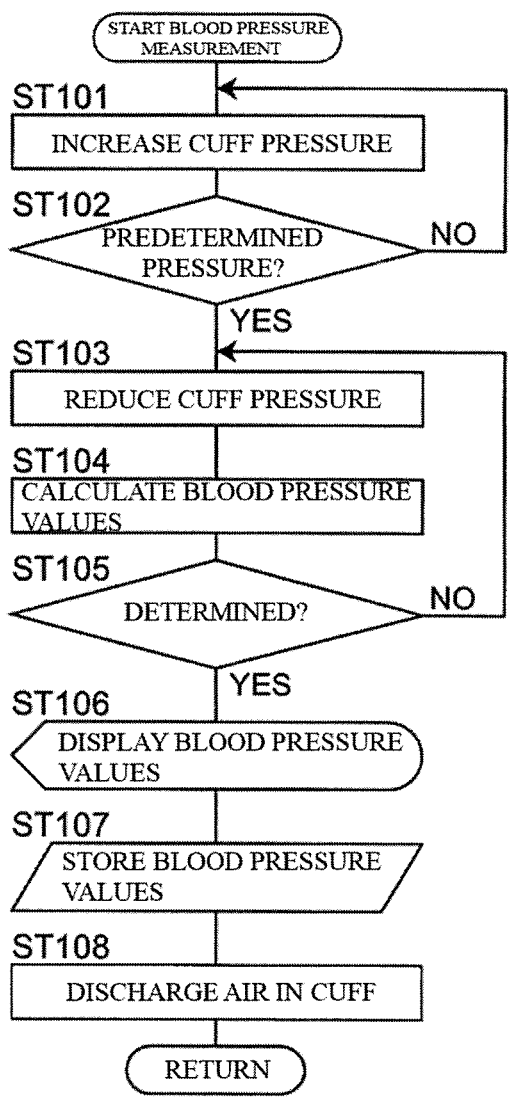
FIG. 4 is a diagram showing an operation flow of the blood pressure monitor.

With the blood pressure monitor 1, the blood pressure values of the measurement subject are measured using an oscillometric method according to the flow shown in FIG. 4 by the CPU 100.

Specifically, if the measurement start switch 52A is pressed (turned on), the blood pressure monitor 1 starts blood pressure measurement as shown in FIG. 4. At the start of blood pressure measurement, the CPU 100 initializes the memory region for processing and outputs a control signal to the valve driving circuit 330. The valve driving circuit 330 opens the valve 33 and discharges the air in the air bladder 22 of the cuff 20 based on the control signal. Next, control for adjusting the pressure sensor 31 to 0 mmHg is performed.

Upon starting blood pressure measurement, first, the CPU 100 closes the valve 33 via the valve driving circuit 330 and thereafter performs control for driving the pump 32 via the pump driving circuit 320 and sending air to the air bladder 22. Accordingly, the air bladder 22 swells and the cuff pressure gradually increases (step ST101). At this time, the segment bladders 41, 42, and 43 that form the air bladder 22 swell due to being inflated to the same pressure.

Upon reaching a predetermined pressure due to the cuff pressure being increased (YES in step ST102), the CPU 100 stops the pump 32 via the pump driving circuit 320 and thereafter performs control for gradually opening the valve 33 via the valve driving circuit 330. Accordingly, the air bladder 22 contracts and the cuff pressure gradually decreases (step ST103).

Here, the predetermined cuff pressure is a pressure that is sufficiently higher than the systolic blood pressure of the measurement subject (e.g., systolic blood pressure +30 mmHg), and is stored in the memory 51 in advance or is determined by the CPU 100 estimating the systolic blood pressure using a predetermined calculation formula while the cuff pressure is being increased (e.g., see JP 2001-70263A).

Also, regarding the deflation speed, a target deflation speed that is a target is set during inflation of the cuff and the CPU 100 controls the opening degree of the valve 33 such that the target deflation speed is reached (see JP 2001-70263A).

In the deflation process, the pressure sensor 31 detects the pressure of the cuff 20 and outputs the cuff pressure signal Pc. The CPU 100 calculates the blood pressure values (systolic blood pressure and diastolic blood pressure) by applying a later-described algorithm through the oscillometric method based on the cuff pressure signal Pc (step ST104). Note that the blood pressure values are not limited to being calculated in the deflation process and may be calculated in the inflation process.

When the blood pressure values are calculated and determined (YES in step ST105), the CPU 100 displays the calculated blood pressure values on the display device 50 (step ST106) and performs control for storing the blood pressure values in the memory 51 (step ST107).

When the measurement ends, the CPU 100 opens the valve 33 via the valve driving circuit 330 and performs control for discharging the air in the air bladder 22 of the cuff 20 (step ST108).

Such measurement is performed repeatedly periodically or as needed. Here, as described above, the three segment bladders 41, 42, and 43 of the air bladder 22 contained in the cuff 20 are integrated. Accordingly, the segment bladders 41, 42, and 43 are not misaligned with each other in the width direction X, for example. As a result, even if the cuff 20 contained in the air bladder 22 is inflated and deflated repeatedly, the flat pressure distribution can be maintained in the width direction X.

Modified Example 1

Figure 11:
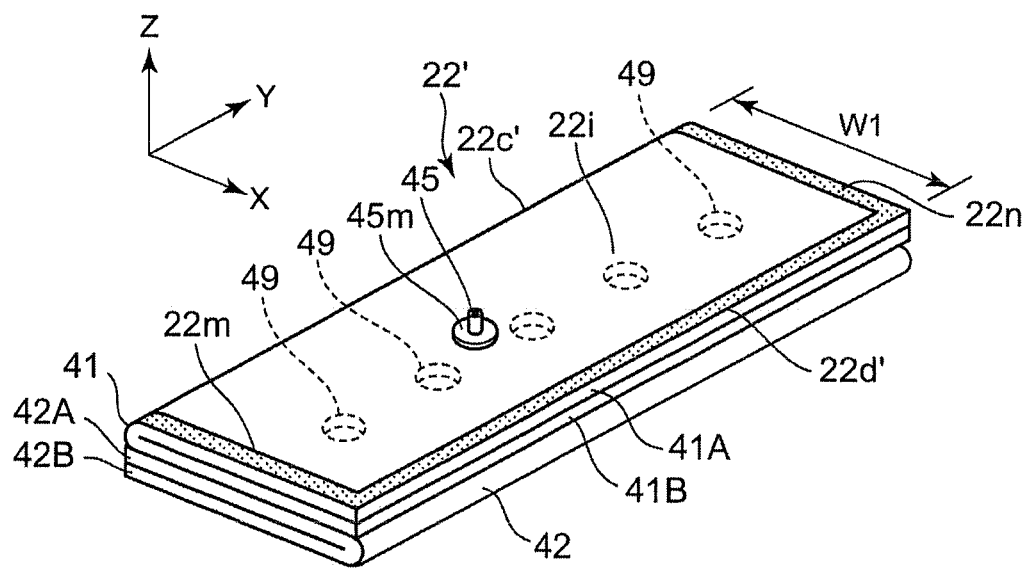
FIG. 11 is a perspective view showing an exterior of another modified example obtained by modifying the air bladder shown in FIG. 7.

In the above-described example, the number of segment bladders stacked in the thickness direction in the air bladder 22 contained in the cuff 20 is odd (three), but there is no limitation to this. For example, as with an air bladder 22' shown in FIG. 11, the number of segment bladders stacked in the thickness direction Z may be even (in this example, two). The air bladder 22' shown in FIG. 11 corresponds to the air bladder 22 shown in FIG. 7 in which the segment bladder 43 is not included and in which the through holes 49' between the segment bladders 42 and 43 are not included. The air bladder 22' is produced through the same procedure as that used to produce the air bladder 22, except that the sheet 43 and the through holes 49' are not included. In FIG. 11, constituent elements that are the same as the constituent elements in FIG. 7 are denoted by the same reference numerals thereas, and detailed description thereof is not included.

Figure 12:
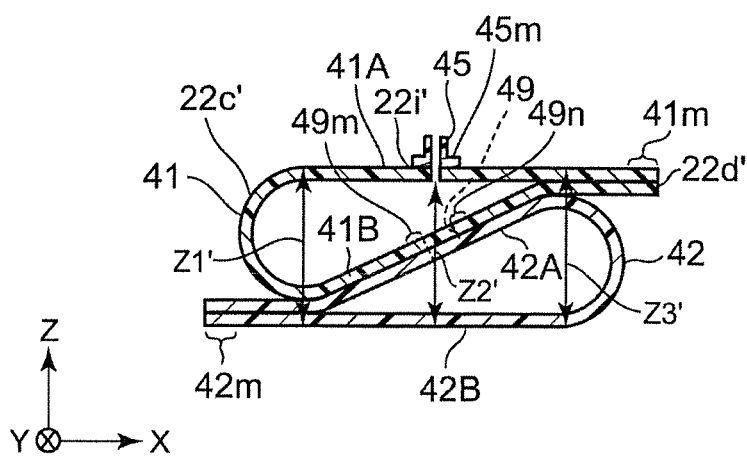
FIG. 12 is a diagram showing a cross-section taken by cutting the air bladder in the width direction X in a state in which a small amount of air has been supplied to the air bladder shown in FIG. 11.

As shown in FIG. 12, if the air bladder 22' is inflated due to a small amount of air being supplied thereto from the outside through the nipple 45, air can flow between the segment bladders 41 and 42 that are adjacent to each other through the through holes 49, and therefore the two segment bladders 41 and 42 are inflated to the same pressure and swell. Note that conversely, the air can be discharged from all of the multiple segment bladders 41 and 42 through the nipple 45.

With the air bladder 22', in the region of the one end side (−X side) 22c' in the width direction X, the relatively thick portion of the segment bladder 41 and the relatively thin portion of the segment bladder 42 adjacent thereto are alternatingly stacked in the thickness direction Z. As a result, in the region of the one end side 22c', the overall thickness Z1' of the segment bladders 41 and 42 is uniform. In the region of the center 22i' in the width direction X of the air bladder 22', the portions with intermediate-level thicknesses of the segment bladders 41 and 42 are stacked. As a result, in the region of the center 22i', the overall thickness Z2' of the segment bladders 41 and 42 is uniform. Also, in the region of the other end side (+X side) 22d' in the width direction X of the air bladder 22', the relatively thin portion of the segment bladder 41 and the relatively thick portion of the segment bladder 42 adjacent thereto are stacked alternatingly in the width direction Z. As a result, in the air bladder 22', the overall thickness Z3' of the segment bladders 41 and 42 is uniform in the region of the other end side 22d'.

Also, in this example, the number of segment bladders 41 and 42 stacked in the thickness direction Z is even (two), and therefore the overall thicknesses Z1', Z2', and Z3' of the segment bladders 41 and 42 are substantially constant in the width direction X.

Figure 15:
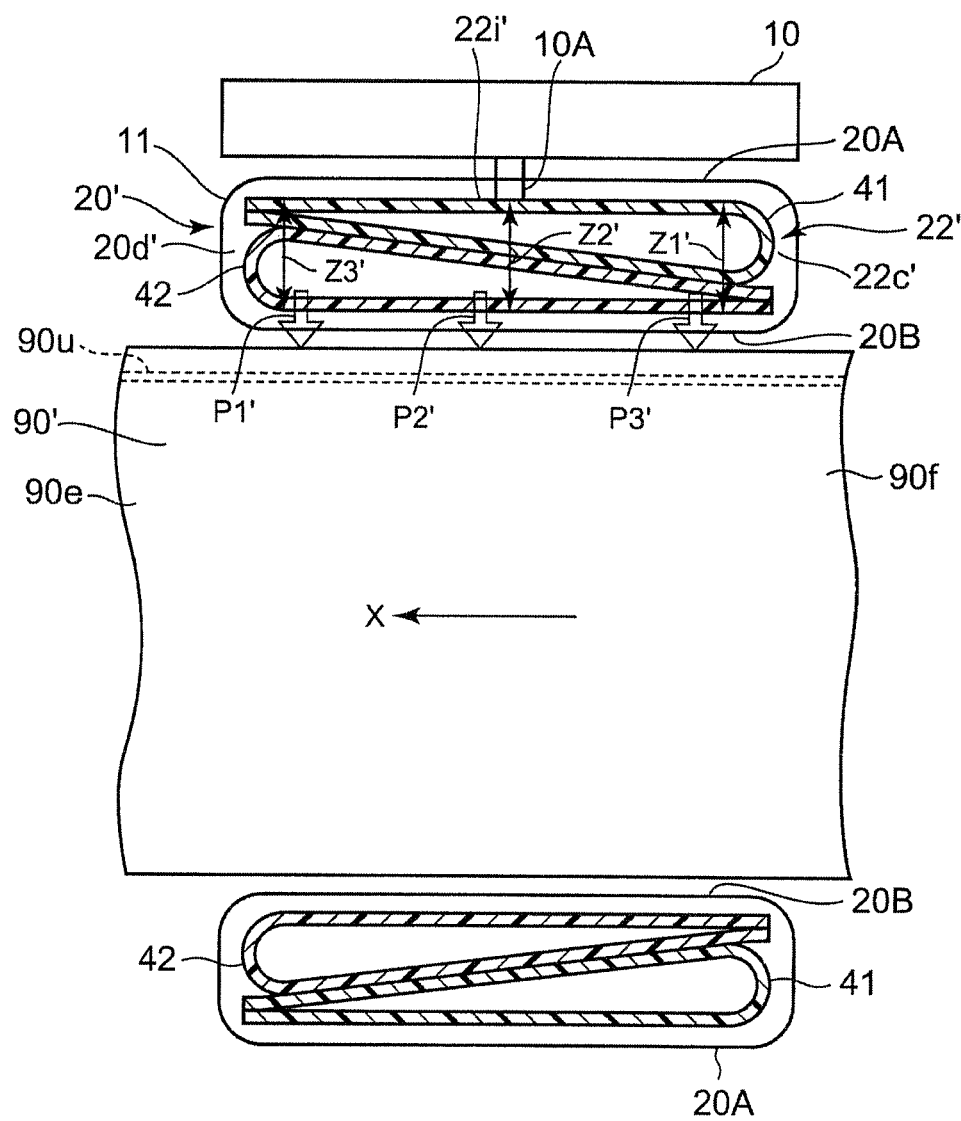
FIG. 15 is a diagram showing cross-section taken by cutting along the artery passing through the wrist, or in other words, a cross-section taken along the width direction X of the cuff, in a state in which the cuff (blood pressure monitor) containing the air bladder shown in FIG. 11 is attached to the wrist.

Accordingly, as shown in FIG. 15, the cuff (indicated by reference numeral 20') containing the air bladder 22' is more easily fit on the outer circumference of the measurement site 90', which has a substantially constant outer diameter in the width direction X. Accordingly, in the width direction X, the pressure distribution on the measurement site 90' is preferably flattened. For example, the pressure P1' in the region of the one end side (−X side) 22c' in the width direction X of the air bladder 22', the pressure P2' in the region of the center 22i' in the width direction X, and the pressure P3' in the region of the other end side (+X side) 22d' in the width direction X can be made approximately equal and the pressure distribution can be flattened. As a result, it is possible to prevent noise from occurring in the cuff pressure signal and the blood pressure value measurement accuracy can be increased.

Also, the two segment bladders 41 and 42 of the air bladder 22' contained in the cuff 20' are integrated, and therefore the segment bladders 41 and 42 are not misaligned from each other in the width direction X, for example. As a result, even if the cuff 20' containing the air bladder 22' is repeatedly inflated and deflated, the flat pressure distribution can be maintained in the width direction X.

Note that the number of segment bladders stacked in the thickness direction Z may be four or more.

For example, if the number of segment bladders stacked in the thickness direction is four, the air bladder is produced as follows. In the above-described FIG. 9A, an additional fourth sheet (denoted by reference numeral 44) is arranged in alignment on the +X side of the sheet 42. Next, similarly to the portions 49m, 49n, 49m', and 49n' that extend in stripe shapes, portions that extend in two stripe shapes along the Y direction (denoted by reference numerals 49m" and 49n") in the approximate center in the X direction of the half-sheet 43B on the +X side of the sheet 43 and the half-sheet (denoted by reference numeral 44A) on the −X side of the sheet 44 are welded and integrated. Next, five through holes (denoted by reference numerals 49", 49", . . . ) are formed at equal intervals along the Y direction in the inner region (excluding the edge portion on the −Y side and the edge portion on the +Y side) between the portions 49m" and 49n" that extend in stripe shapes, of the half-sheet 43B on the +X side of the sheet 43 and the half-sheet 44A on the −X side of the sheet 44. Thereafter, when the even-numbered sheet 42 is folded in half toward the side opposite to that of the odd-numbered sheets 41 and 43 as shown in FIG. 9B, the sheet 44 is also folded in half to the side opposite to that of the odd-numbered sheets 41 and 43. Then, as shown in FIG. 9C, the edge portions 42c and 42d on the side opposite to the folding location 42b for folding in half of the sheet 42 are welded together (the welding location is denoted by reference numeral 42m), and the edge portions on the side opposite to the folding location for folding in half of the sheet 44 are welded together. Thereafter, when the edge portions on the −Y side and the +Y side of the half-sheets forming the sheets 41, 42, and 43 are collectively welded in the thickness direction Z, the edge portions on the −Y side and the +Y side of the half-sheets forming the sheet 44 are also welded. In this manner, an air bladder including four segment bladders stacked in the thickness direction Z is produced.

If the number of segment bladders stacked in the thickness direction Z is five, an additional fifth sheet is further arranged in alignment on the +X side of the sheet 43 in the above-described FIG. 9A. Also, as described above, integration of the half-sheets that overlap with each other, formation of through holes in the inner region of the half-sheets that overlap with each other, folding in half of the sheets, welding of the edge portions on the sides opposite to the folding locations for folding in half, and collective welding of the edge portions on the −Y side and the +Y side are performed. In this manner, the number of segment bladders stacked in the thickness direction Z can be increased.

Modified Example 2

Figure 10:
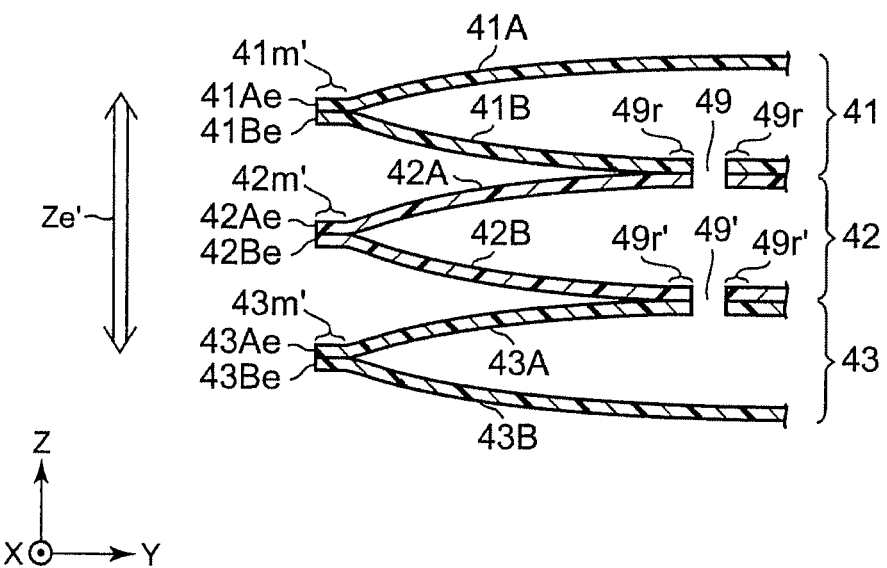
FIG. 10 is a diagram showing a cross-section of a modified example obtained by modifying the air bladder shown in FIG. 7.

In the above-described example, as shown in FIG. 8B, the edge portions on the −Y side (the same applies to the edge portions on the + side as well) in the lengthwise direction Y of the air bladder 22 are collectively welded, but there is no limitation to this. For example, as shown in FIG. 10, the edge portions 41Ae and 41Be on the −Y side of the half-sheets 41A and 41B forming the segment bladder 41, the edge portions 42Ae and 42Be on the −Y side of the half-sheets 42A and 42B forming the segment bladder 42, and the edge portions 43Ae and 43Be on the −Y side of the half-sheets 43A and 43B forming the segment bladder 43 may be respectively welded separately.

In such a case, the stroke amount (swelling distance) Ze' in the thickness direction Z is increased at the edge portion on the −Y side (the same follows for the edge portion on the + side as well) in the lengthwise direction Y of the air bladder 22, and thus the wrist 90 can be compressed.

Note that if this configuration is used, the loop-shaped portions around the through holes 49 of the half-sheets 41B and 42A are welded together in advance, for example (the welding location is denoted by reference numeral 49r), in order to prevent leakage of air from the through holes 49 through the gap between the half-sheets 41B and 42A that are adjacent to each other. Also, the loop-shaped portions around the through holes 49 of the half-sheets 42B and 43A are welded together, for example (the welding location is denoted by reference numeral 49r'), such that leakage of air from the through holes 49' through the gap between the half-sheets 42B and 43A that are adjacent to each other is prevented.

Verification Test

Figure 16:
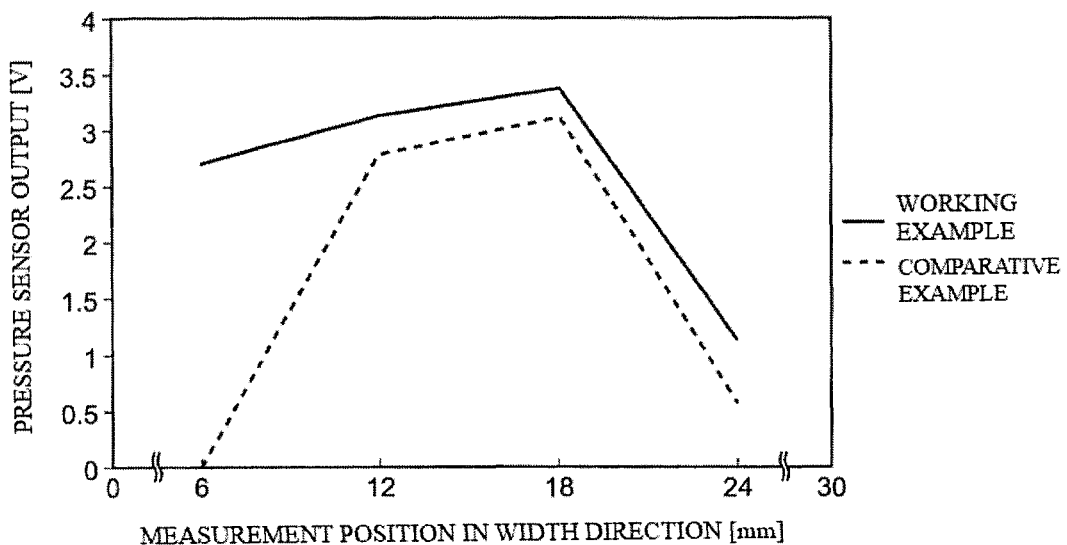
FIG. 16 is a diagram showing a comparison of a pressure distribution in the width direction of the air bladder (Working Example) shown in FIG. 11 and a pressure distribution in the width direction of an air bladder (Comparative Example) composed of one bladder, at a time of performing a verification test.

FIG. 16 shows a comparison of a pressure distribution in the width direction of the air bladder shown in FIG. 11 (indicated as "Working Example" by the solid line in the drawing) and a pressure distribution in the width direction of an air bladder composed of one bladder (indicated as "Comparative Example" by the broken line), when a verification test has been performed.

Here, the air bladder of the "Comparative Example" is formed by opposing two half-sheets, welding the edge portions in the width direction together, and welding the edge portions in the lengthwise direction orthogonal to the width direction together. A nipple for introducing and/or discharging a fluid is attached to one half-sheet.

The above-described air bladder of the "Working Example" and the air bladder of the "Comparative Example" are both set such that the overall dimension in the width direction is 36 mm. Also, the width direction dimension of the welding locations (welding gussets) on both side are each set to be 3 mm. In other words, the 30-mm portions in the width direction of the air bladder of the "Working Example" and the air bladder of the "Comparative Example" are both set as regions that can swell in the thickness direction Z.

The horizontal axis in FIG. 16 indicates the measurement positions in the width direction of the above-described air bladder of the "Working Example" and the air bladder of the "Comparative Example". In this example, the locations of the marks 6 mm, 12 mm, 18 mm, and 24 mm in the region of the air bladder that can swell (the marks on the two ends thereof are for 0 mm and 30 mm) are the measurement positions. The vertical axis in FIG. 16 denotes the outputs of pressure sensors that are respectively arranged at the above-described measurement positions in the air bladder of the "Working Example" and the air bladder of the "Comparative Example". The outputs of the pressure sensors (in units of volts [V]) are proportional to the pressures at the locations at which the pressure sensors are arranged in the air bladders.

In the verification test, the air bladder of the "Working Example" and the air bladder of the "Comparative Example" are inflated to about 300 mmHg in parallel simultaneously by the same inflation source. As can be understood from FIG. 16, the above-described air bladder of the "Working Example" has a pressure distribution that is flatter in the width direction in comparison to the air bladder of the "Comparative Example". Thus, the effect of one or more embodiments of the present invention was verified through the verification test.

In the above-described embodiment, the measurement site was mainly the wrist 90, but there is no limitation to this. The measurement site may be another site, such as an upper arm.

Also, in the above-described embodiment, the blood pressure measurement cuff was of a type that is attached around the measurement site by being folded over using a ring, but there is no limitation to this. The blood pressure measurement cuff may be of a type that is attached around the measurement site by being wrapped in one direction in a spiral form.

Also, in the above-described embodiment, the blood pressure measurement cuff was formed by an air bladder serving as a fluid bladder being contained in a band-shaped body. However, there is no limitation to this. The fluid bladder may be composed of elastomer, for example, and the fluid bladder itself may form the blood pressure measurement cuff.

Also, the fluid was air, but there is no limitation to this. It is sufficient to use a fluid that can inflate or deflate a fluid bladder, such as nitrogen.

Also, instead of welding a sheet and a nipple and portions of sheets, adhesion of these portions may be performed using adhesive, for example.

The above-described embodiments are exemplary and various modifications are possible without departing from the scope of the invention. The multiple above-described embodiments can be achieved independently, and it is also possible to combine embodiments. Also, the various features in the different embodiments can be achieved independently, and it is also possible to combine features in different embodiments.

REFERENCE SIGNS LIST

1 Blood pressure monitor
10 Main body
20, 20' Cuff
22, 22' Air bladder
41, 42, 43 Segment bladder
45 Nipple

The invention claimed is:

1. A fluid bladder provided in a blood pressure measurement cuff in order to compress a measurement site, comprising:
    a plurality of segment bladders comprising at least first, second, and third segment bladders which are formed by first, second, and third sheets of equal rectangular size such that:
        a portion of a first-half of the second sheet overlaps with a portion of a second-half of the first sheet; a portion of a second-half of the second sheet overlaps with a portion of a first-half of the third sheet; each of the overlaps is at least partially but firmly fixed by welding or adhering;
        thereafter, the first sheet is folded to place its free-end side on top of its opposite-end side where the overlap exists, so as to define a first tube; the third sheet is folded to place its free-end side on top of its opposite-end side where the overlap exists, so as to define a third tube; the second sheet is folded to place its one-end side where the overlap with respect to the first sheet exists on top of its other-end side where the overlap with respect to the second exits, so as to define a second tube; and
        opposite ends of each of the first, second, and third tubes are closed by welding or adhering,
    wherein the plurality of segment bladders are stacked in a width direction orthogonal to the measurement site and integrated, and folding locations are arranged alternatingly on opposite sides in the width direction.

2. The fluid bladder according to claim 1,
    wherein through holes that enable air to flow between segment bladders that are adjacent to each other are provided in inner regions of half-sheets that are adjacent to each other in the segment bladders that are adjacent to each other, and
    wherein the half-sheets that are adjacent to each other are integrated by being welded or adhered such that the through holes are surrounded.

3. The fluid bladder according to claim 2, wherein a nipple for introducing and/or discharging fluid for compressing the measurement site is attached to a half-sheet of the plurality of segment bladders that is arranged on a side located farthest from the measurement site.

4. The fluid bladder according to claim 1, wherein a number of segment bladders stacked in a thickness direction is even.

5. The fluid bladder according to claim 1, wherein a number of segment bladders stacked in a thickness direction is odd.

6. A blood pressure measurement cuff including the fluid bladder according to claim 1.

7. A blood pressure monitor comprising the blood pressure measurement cuff according to claim 6 and a main body including an element for blood pressure measurement.

8. A blood pressure measurement cuff including the fluid bladder according to claim 2.

9. A blood pressure measurement cuff including the fluid bladder according to claim 3.

10. A blood pressure measurement cuff including the fluid bladder according to claim 4.

11. A blood pressure measurement cuff including the fluid bladder according to claim 5.

* * * * *